(12) United States Patent
Daglow et al.

(10) Patent No.: US 12,350,486 B2
(45) Date of Patent: Jul. 8, 2025

(54) APPARATUS AND DEVICE TO FUNCTION AS AN ELECTRICAL LEAD CONSISTING OF ELECTRODES FOR NEUROLOGICAL STIMULATION AND SIGNAL RECORDING

(71) Applicants: Terry Daglow, Houston, TX (US);
Joseph Johnnie, Pearland, TX (US);
John Proctor, Houston, TX (US)

(72) Inventors: Terry Daglow, Houston, TX (US);
Joseph Johnnie, Pearland, TX (US);
John Proctor, Houston, TX (US)

(73) Assignee: LSDM LABS, LLC, Houston, TX (US)

( * ) Notice: Subject to any disclaimer, the term of this patent is extended or adjusted under 35 U.S.C. 154(b) by 206 days.

(21) Appl. No.: 18/349,720

(22) Filed: Jul. 10, 2023

(65) Prior Publication Data
US 2024/0009449 A1 Jan. 11, 2024

(51) Int. Cl.
*A61N 1/02* (2006.01)
*A61B 5/24* (2021.01)
*A61N 1/04* (2006.01)
*A61N 1/05* (2006.01)
*B33Y 70/00* (2020.01)
*B29C 64/209* (2017.01)
*B33Y 30/00* (2015.01)

(52) U.S. Cl.
CPC .............. *A61N 1/0488* (2013.01); *A61B 5/24* (2021.01); *A61N 1/0534* (2013.01); *B33Y 70/00* (2014.12); *A61N 1/0541* (2013.01); *A61N 1/0543* (2013.01); *A61N 1/0551* (2013.01); *B29C 64/209* (2017.08); *B33Y 30/00* (2014.12)

(58) Field of Classification Search
CPC .................... A61B 5/14532; A61B 5/14865
See application file for complete search history.

*Primary Examiner* — Michael J D'Abreu
(74) *Attorney, Agent, or Firm* — Greenberg Traurig, LLP

(57) ABSTRACT

A device and method consisting of conductive, non-conductive, and support materials. These materials when dispensed or extruded onto a multitude of temporary structures will create an implantable conductive and non-conductive structure suitable for neurological electrical stimulation and neurological electrical recording. This structure may also be suitable for delivering fluid and/or contain optical structures suitable for physiological sensing.

10 Claims, 20 Drawing Sheets

APPARATUS AND DEVICE TO FUNCTION AS AN ELECTRICAL LEAD CONSISTING OF ELECTRODES FOR NEUROLOGICAL STIMULATION AND SIGNAL RECORDING

CROSS-REFERENCE TO RELATED APPLICATIONS

This application is a divisional application of U.S. patent application Ser. No. 16/478,762, filed on Jul. 17, 2019, which is a National Stage application of PCT International Patent Application Number PCT/US2018/014117, filed on Jan. 17, 2018, which claims priority to U.S. provisional application 62/447,223, filed on Jan. 17, 2017, all of which are herein incorporated by references in their entirety.

FEDERAL FUNDING LEGEND

This invention was not created using federal funds.

FIELD OF THE INVENTION

The present invention relates to an electrical pulse generator or "electroceutical" device to stimulate and override the human body's nervous system through neuromodulation generally and a pulse generator and one or more uniquely designed leads offering greater biocompatibility and flexibility through a novel construct, materials and method of manufacture to more accurately and effectively deliver neurological modulation, stimulation, and recording.

BACKGROUND

Neurostimulation devices, in essence, generate electrical impulses and deliver those impulses to specifically designated areas (e.g. nerve tissue of the deep brain, vagus nerve, spinal cord and sacral nerves, etc.) throughout the body. In addition, the production of an electromagnetic field created in the area of the electrical impulses, affecting the behavior of charged objects (i.e. charged ions) in the vicinity of the field which results in the propagation of wavelike impulses to the affected tissue. Utilized in the FDA approved treatment of a myriad of neurological disorders, neurostimulation has been applied through (1) deep brain stimulation (DBS) (treating conditions ranging from Parkinson's Disease, dystonia, essential tremor, and epilepsy, depression and obsessive-compulsive disorder), (2) vagus nerve stimulation (remediating the effects of depression and epilepsy), (3) spinal cord stimulation (SCS)(decreasing and eliminating pain), and (4) sacral nerve stimulation (remedying urinary and fecal incontinence). Further, studies suggest that Neurostimulation may equally have applications in obesity, stroke recovery, Alzheimer's Disease, anxiety, bulimia, tinnitus, traumatic brain injury, Tourette's Syndrome, sleep disorders autism and bipolar disorder (through deep brain stimulation), epilepsy (via cortical stimulation), migraines and extremities pain (through peripheral nerve stimulation), hypertension (through carotid arteries and sinus stimulation), sleep apnea (via hypoglossal and phrenic nerve stimulation), angina and asthma (through spinal cord stimulation), and obesity, bulimia, and interstitial cystitis (via gastric stimulation and/or sacral and pudendal nerve stimulation).

Yet, as the indications for neurostimulation continue to expand, the technology developed to potentiate the electrical impulse from the generator to the lead continues to revolve around an antiquated system that implements use of wire as the primary conduit of electricity. Current devices are constructed of polymers, metallic wires and machined or extruded metallic components. The metallic materials are joined via resistance spot welding, laser welding, crimping or swaging. Expressly, the existing state of the art offers variations based on the use of metal wires in an array of configurations including coil designs (coil structure with 4-electrode leads), unconstrained leads (straight wire with 8-electrode leads), independent leads: straight wire with 8 and 16-electrode leads, and coil in coil design (dual coil construction with 8 and 12 electrode leads)—each of the which suffers from the same infirmities of (a) stiffness, (b) low or no stretch, (c) bio-incompatibility, (d) degradation over time, (e) surgical placement and implantation anchoring that requires a highly-skilled physician, (f) high incidences of surgical revision, (g) migration, (h) breakage, and (i) expensive and complicated manufacturing processes. It is the goal of the present invention to address these shortcomings ergonomically, economically and materially.

In general, the present invention provides a device and method for use incorporating a novel arrangement of conductive and nonconductive materials integrally assembled into an apparatus utilizing methods of additive manufacturing (e.g. three-dimensional printing) that produces a "soft" polymer, body-compliant lead that is easily and highly stretchable in a manner that more closely resembles and mimics natural human tissue. Moreover, the present invention offers a simple, homogeneous construction of conductive and non-conductive polymer materials that presents improved performance and compatibility of electrode/tissue interface, body accessibility for high mobility and a high degree of utility in complex clinical applications. Finally, the method for producing the proffered device lends itself to a system of manufacture that may be used for the creation of custom leads that can be derived rapidly for patient specific applications or for the creation and deployment in simple to complex animal models. While the resulting electrical device will resemble the functioning of current devices, its unique design and method of assembly represents a significant development of an entirely new level of functionality and performance in neurological modulation, stimulation, and recording as yet unrealized.

At a minimum the present invention will allow for better functioning and improved utilization of the existing technology and, at most, will afford researchers and clinicians alike the opportunity to accelerate neuroscientific discoveries, research and development to unimagined heights. Specifically, the invention will allow for more rapid and enhanced anatomical access to sites in the nervous system which will in turn facilitate the implementation of research projects, neuro-technology development, and clinical therapy deployments.

Ultimately, the expedient access and exceptional implantations afforded by this invention will expedite neurological discovery, advance nervous system integration with technology, and enhance our understanding of the human brain. In essence, the technology that is the present invention will allow us the opportunity to augment the human neuro-electric system to the benefit of the entire body.

BRIEF SUMMARY OF THE INVENTION

The device that is the present invention incorporates a unique design and additive manufacturing of a device that elicits improved device functionality coupled with an individualized, "on-demand" procurement process. Via the application of liquid polymers through a moveably positioned extruder directed about a rotational axis in a threeplane configuration, the construction of an electrically conductive and non-conductive matrix is not only biocompatible and malleable but also more elastic, durable, and easily maneuverable and amendable to secure placement.

The most common application for the device itself is an implantable medical device assembly, such as a neurostimulator, comprised of a lead or electrode for conducting electrical signals and a programmable signal generator or power source to provide the signal pulse to the lead or leads. Such a device may be developed and produced for a wide range of applied and theoretical therapeutic interventions including brain stimulation, deep brain stimulation, transcranial stimulation, spinal cord stimulation, transcutaneous supraorbital nerve stimulation, cochlear implantation, retinal stimulation, cortical stimulation, cardiac electrostimulation, vagus nerve stimulation, sacral and pudendal nerve stimulation, hypoglossal and phrenic nerve stimulation, and gastric stimulation. For the purpose of this invention the present disclosure focuses on devices used for neurological stimulation, modulation and recording through leads and/or electrodes, and a power source, in general, while contemplating use in each of the aforementioned applications and other applications not yet devised. The device, when assembled with a stylet used for support and guiding placement of the device, may then be placed into the desired anatomical area of interest for electrical field propagation.

Away from the conductive/non-conductive arrangement of the present device, the additional claimed advantage of a manufacturing apparatus and means for production can best be viewed and understood by observing the fused deposition modeling (FDM) method of lead construction and method of additive manufacturing, tempered with the several key differences and advancements of the present invention. Like FDM, the present invention utilizes technology similar to FDM additive manufacturing (AM) to lay down material in layers, in a solid material based AM technology by extruding small flattened "strings" of molten material to form sequential layers (as the material hardens immediately after extrusion from the nozzle). Unlike FDM, though, this present invention extends the current perpendicular and planar build (exhibiting a gantry design for movement mostly in the horizontal X & Y directions with a slow climb in the Z direction as the piece is "printed" or formed) to a three dimensional, fully customizable build surface or substrate while maintaining 3 axis positioning (X, Y and Z axes) coupled with additional rotational axes. The material deposition head, via deposition of a liquid or semi-solid material through the extruder or extrusion head), deposits material through, or extrudes through, the nozzle or tip of the head. What is more, the extrusion head may incorporate one or two additional axes of rotation typical of 5-axis CNC machining equipment. These additional axes are either an A or B axis (about the X or Y axis respectively) and a C axis (about the Z axis) and the build structure, adhered around the substructure for the electrical device, which is freely rotatable in an additional axis (Ø) parallel to the X axis. Also, the build structure may be mounted to a horizontal base or table that may also be motion controlled in X, Y, and Z axes, and/or rotationally in a B axis, as dictated by the desired device design and configuration, to complete movements in conjunction with (i.e. in concert with) the deposition head.

The rotationally active application substrate (i.e. the three-dimensional build substructure, substrate, or surface) can be as simple as a wire suspended between two supporting points or a mandrel which may be made to rotate by numerically controlled motors. These points can be collets or chucks suitable to retain and support the wire. These points might also be mechanically linked together and rotated by a single numerically controlled motor. This build substructure may have segments which utilize fully customized multi-planar and multi-segmented substructures that may be a cylindrical rod or mandrel to facilitate the application of an extruded medium of polymeric material (i.e. liquid silicon rubber) consisting of conductive and non-conductive polymers of which each set of polymers are suitable for human and animal implantation.

Conductive polymer is applied to the build substrate to provide a continuous conductive path for electrical impulses between the proximal termination element, also known as a contact band, and the distal stimulation or recording element, also known as an electrode. These polymers can be one part or multi-part materials and may be cured via air, heat, ultra-violet (UV) light or infra-red (IR) light or any combination thereof. Non-conductive polymer is interspersed between the continuously conductive polymer elements to act as an insulator to separate electrical impulses.

The principal or base polymer used to produce the device may be liquid silicone rubber (LSR) or other polymeric material displaying similar characteristics or properties. The deposition head nozzle may offer provisions for thermal temperature control suitable to manage the transfer of thermal energy to specific locations within the nozzle design in order control material flow and curing parameters (including curing time, curing rate, and prohibitive measures to avoid premature curing and nozzle clogging).

In addition to thermal temperature controls, the deposition head and nozzle may further encompass provisions for light energy transmission where the light energy transmitted to the curing material exhibits variable and controllable intensity, from a single wave length to a combination of wavelengths (from infrared to ultraviolet as is suitable to cure the material). To simplify description of the invention, and by way of example, we will refer to this light as UV light although other forms of light may be selected without departing from the scope of the invention.

In a preferred embodiment, the present invention includes a device and method of manufacture of a lead, electrode, and/or a recording lead exhibiting alternating conductive and non-conductive elements encapsulated in a non-conductive, biocompatible shell that are applied and adhered to a rotationally moveable substructure or substrate and cured using a UV light curing process. UV light can flood the work area or be selectively focused to start the curing process just prior to entering the extrusion head or while in the extrusion head from the extrusion head. This focused UV light can also be delivered at the extrusion head or nozzle, just prior to making contact with the platen or previous polymer build layer or surface. The invention assumes that a UV-LSR (ultraviolet cured liquid silicone rubber) extruded material, for example, will require its cure cycle to initiate before it is deposited onto the substructure substrate or previous polymer build layer in order to minimize flow after deposition and maximize dimensional stability of the device. A Print ID marker and labeling into the lead, using radio-opaque material may also be accomplished at this stage or another subsequent stage as desired. This invention may also include one or more additional extruders and/or co-extruders to be used in conjunction with the described extruders that deposit polymer for the device. The purpose of these additional extruders would be to deposit separate material that can serve as support structures to maintain the dimensionality and physical stability of the device polymer material as it cures. Extruders that deposit this support material may deposit multiple materials and/or incorporate features which allow for catalysis of a dissolution process within the support material itself. For example, a cylindrical extruder within another cylindrical extruder could deposit an internal material inside of an external material, such that the internal material dissolves the external material over a period time where that period of time in which the material dissolves could vary depending on the application, ranging from completion of the device build to a full life span of usage. This process allows for the creation of cavities, voids, or channels within the device that have fluid/drug delivery, tissue engineering applications (for example tissue ingrowth), and for light conduction features to be added or inserted, such as optical fibers or other optically performing material which fills the cavity to support certain optogenetic applications.

Similarly, this coextrusion method would allow for extruding two or more types of conductive polymeric compounds such as to construct continuous conductive elements with unique electrical performance characteristics or properties.

The rotational motion and angular orientation of the substrate or mandrel can be used to control the growth and direction of the cavities and channels within the support material to fit the potential application. Additionally, optical fibers may be incorporated into the device to support optogenetic or other channel requiring applications (e.g. drug delivery). Such fibers would be inserted in some manner during the build process and polymer or UV-LSR would encapsulate support structures, fiber optics, or other channels in the device. Such additions could run longitudinally in the device. Tubular additions could also enter and exit the device at different points and angles providing variable trajectories and exit orifices. Channels may terminate at any point proximally or distally from the device. At the proximal end, fiberoptic containing channels may connect with an optical connector or connectors, and at the distal end of the device may terminate in such a way as to deliver light appropriately for optogenetic function, may create terminal anchoring structures, or may create drug delivery channels running throughout.

In essence, the most novel features of this invention include a design, made possible by a method of additive manufacture from biocompatible conductive and non-conductive polymer materials, a completed lead device that is: 1) 100% comprised of biocompatible soft polymer materials, 2) that is suitable for chronic, long-term implantable use, 3) that is highly elastic and body compliant, and 4) that integrate connector and electrode features and their respective conductive pathways, distal to proximal end, into single elements made of a homogeneous conductive polymer material.

BRIEF DESCRIPTION OF THE DRAWINGS

FIG. 1c details the cylindrical rod-shaped build substrate depicted in FIG. 1a.

FIG. 1d details the nozzle depicted in FIG. 1a.

FIG. 2b details components of the complete assembly in FIG. 2a.

FIG. 3a illustrates the first constructed application layer for the example device in FIG. 2a.

FIG. 3c illustrates the third constructed application layer for the example device in FIG. 2a.

DETAILED DESCRIPTION OF THE INVENTION

Figure 1A:
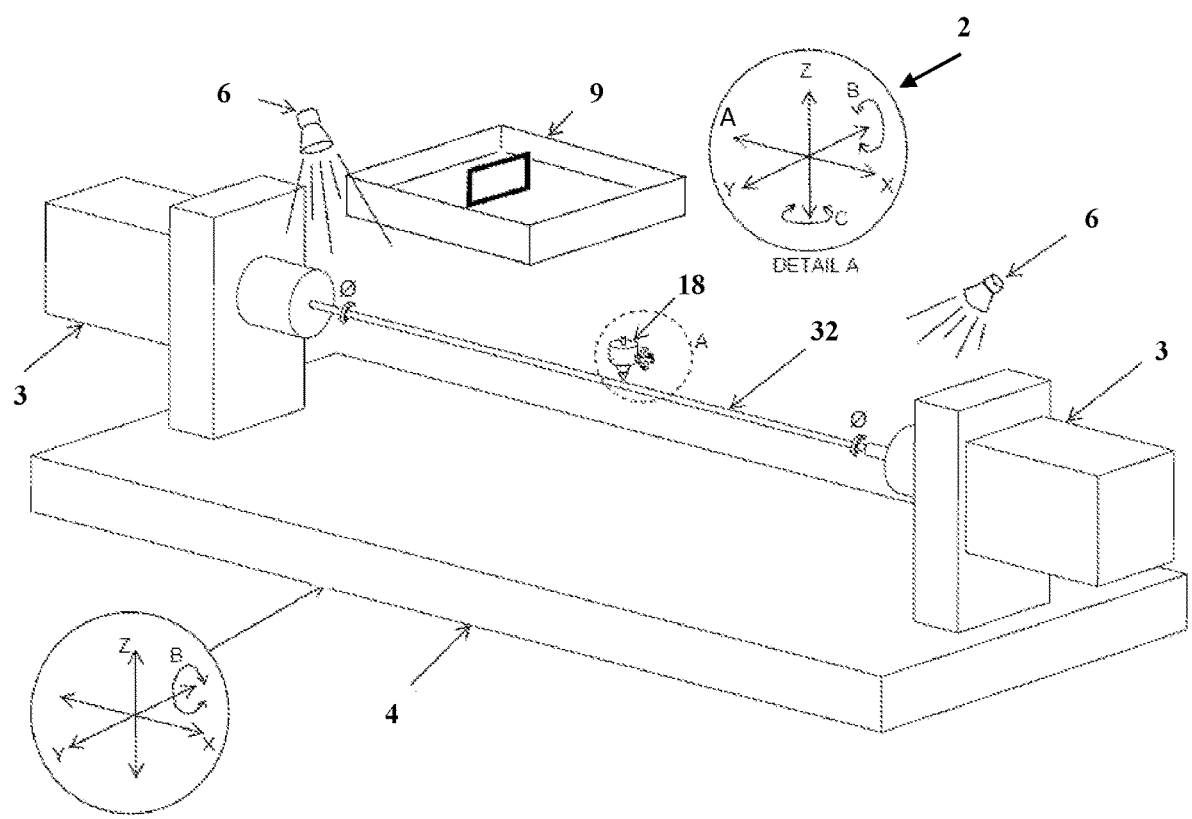
FIG. 1a shows an apparatus for depositing material including a cylindrical rod-shaped build substrate, a mechanism for rotating the build substrate mounted to a base or table, and a motion controlled nozzle.

Referring to FIG. 1a, the present invention is depicted including a cylindrical rod-shaped build substrate or mandrel 32, a motion controlled nozzle 18 for depositing material, a means of controlling the rotational motion of the build substrate about its centerline 3, a base or table 4 that may be fixed or optionally motion controlled.

The apparatus that is the present invention may incorporate more than 1 nozzle 18, a minimum of 2 nozzles 18, or a plurality of nozzles, extruders, or coextruders, 18 for the purposes of depositing, in an alternating manner, materials with differing properties, either electrically conductive or non-conductive, so as to create electrically conductive pathways.

The nozzle 18 is motion controlled to move in at least 3 axes 2 (i.e. the X axis, the Y axis, and the Z axis). The X axis is horizontal and parallel to the centerline of the cylindrical build substrate 32, the Y axis is horizontal and perpendicular to the X axis and the Z axis is vertical and orthogonal to both the X and Y axes. Additionally, the nozzle may be controlled in a 4th and 5th rotational axis similar to 5 axis CNC machining equipment. If a 4th axis is employed, it shall be rotational about the X or Y axis and shall be named the A or B axis respectively. If a 5th axis is employed it shall be rotational about the Z axis and shall be named the C axis. The rotational axis for the build substrate is named the theta (Ø) axis and its motion shall be numerically controlled. The provision for Ø axis motion control is controlled by 2 independent servo motors at each end of cylindrical rod-shaped build substrate or mandrel 32. Alternatively, a single motor may be used to drive each end dependently.

The build area mechanism itself is attached to a base or table 4 which may be fixed or may be motion controlled in 3 similar linear planes (e.g. axes X, Y, and Z). In relation to the build area, an optical or mechanical distance sensing and measurement system will be employed to control the distance of the nozzle 18 tip from the build substrate 32. Such a system will provide closed loop control to the motion control system to account for deflection of the build substrate (or mandrel, or wire, etc.) as it deflects due to gravity and the buildup of material mass applied to the build substrate 32. This deflection will likely increase continuously and non-linearly as the build progresses, and vary non-linearly over the length of the mandrel 32. Because this variability will be difficult to account for numerically in the build sequence program, a closed loop control system will be employed to continuously adjust the position of the nozzle 18 to allow for this variation as the device is constructed. The action of this control may be on the head or on the table or base 4 to which the mandrel 32 rotational support system is attached.

Because of the variability due to mass and the effects of gravity, and because of the mass flow properties of fluid in a gravitational field, a zero or lower gravity environment would be well suited for dimensional control of the of devices constructed and for operation of the necessary apparatus, both embodied herein. Thus, it is anticipated that the construction method and device itself can be improved upon if the apparatus is able to operate, and designed for operation, in low or zero gravity environment.

As depicted in FIG. 1*a*, a waste material station 9 is provided for in the apparatus for deposition of over cured (hardened) or under cured (liquid) material which cannot be used or can no longer be used in the construction of the device. The station 9 will also be used to purge and/or clean the nozzle of unusable material.

The build area may be provisioned with UV light sources 6 to support continuous curing of deposited material.

Figure 1B:
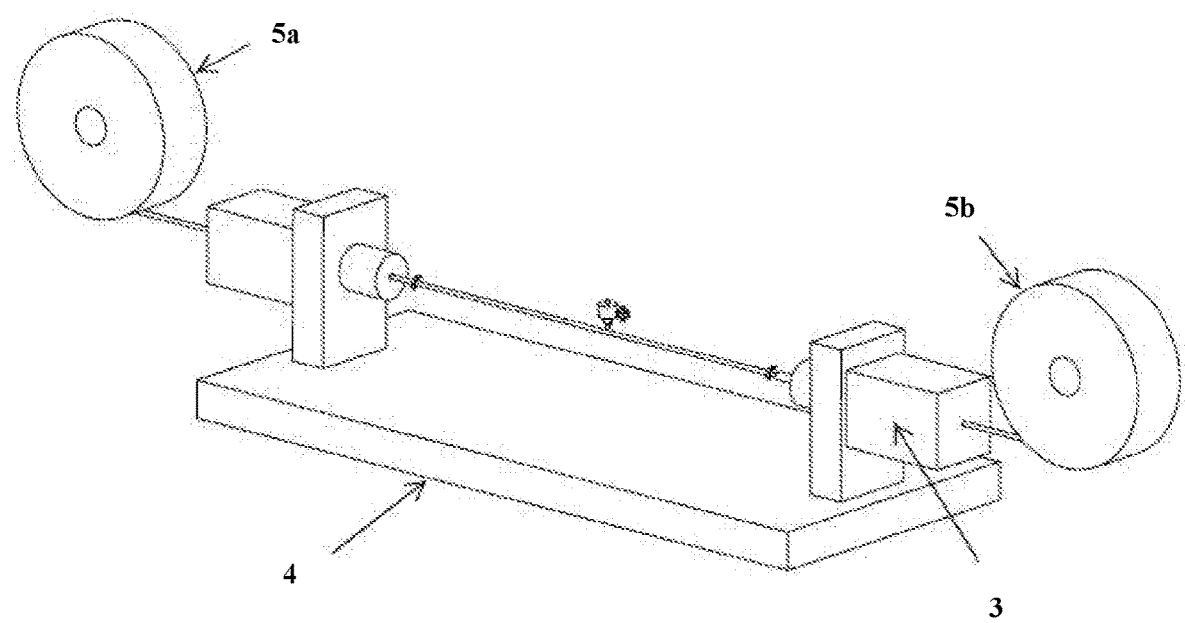
FIG. 1b shows a supply and take up reel system which can rotate to control a continuous length wire or rod build substrate.

FIG. 1*b* depicts one embodiment for continuous length production for constructs which exceed the physical limits of the build space and therefore must be accepted and wound at a receiving station that may be at either end of said build space and may be equally or unequally received at either end of the rotating mandrel 32. By comparison, the apparatus in FIG. 1*a* is intended to produce a lead body or device of discrete length (i.e. the length of the supporting and rotating mandrel 32).

These receiving stations may be fixed in relation to the mounting table 4 or unassociated with the mounting table 4 where the receiving stations move in concert with the apparatus or independent of the apparatus and is likewise motion controlled in 3 similar linear axes X, Y, and Z.

In another embodiment, the apparatus incorporates a supply reel 5*a* and a take-up reels 5*b* which are able to rotate about the Ø axis. The supply reel may contain any type of wire or rod material suitable for a build substrate where at least 2 pulleys are used to guide the wire/rod and are fixed such that the wire/rod centerline remains fixed in space, e.g. it does not move along any other axis as it is rotated during the build process. This take up reel 5*a* and supply reel 5*b* assembly shall be rotationally motion controlled about the Ø axis. The reels are also rationally controlled numerically about their respective hub centers such that the wire/rod may be fed forward or backward and wound about the reels much in the same way as a film projector is able to play or move the film forwards and backwards in an effort to achieve the desired device construct, current, channel designation, or the like.

Figure 1C:
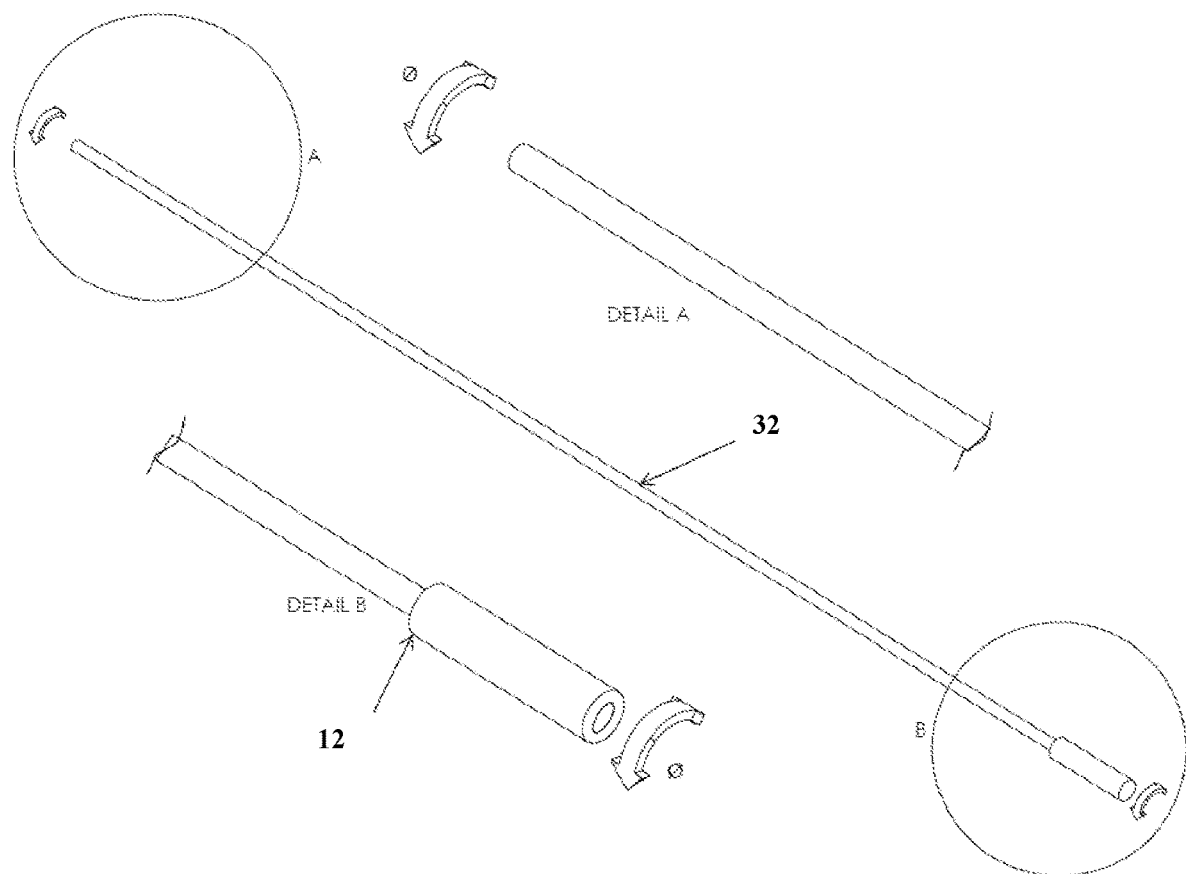

As represented in FIG. 1*c*, a build substrate or mandrel 32 is suitable to perform as a build substrate or mandrel 32 and as a support element for the device in process and after final construction or assembly. This mandrel 32, alternatively referred to as the 'build substrate' or 'build surface', may be constructed of solid metallic wire, braided wire, or extruded wire rod depending on required functionality. The surface of the mandrel is sufficiently smooth to "release" from the device inner surface after the device is created around it and is made to manifest an outside diameter which shall define the inside diameter of the device that is constructed. It may be necessary for the build substrate or mandrel 32 to have a shoulder or larger diameter 12 at some station along its length to support the formation of the device.

Figure 1D:
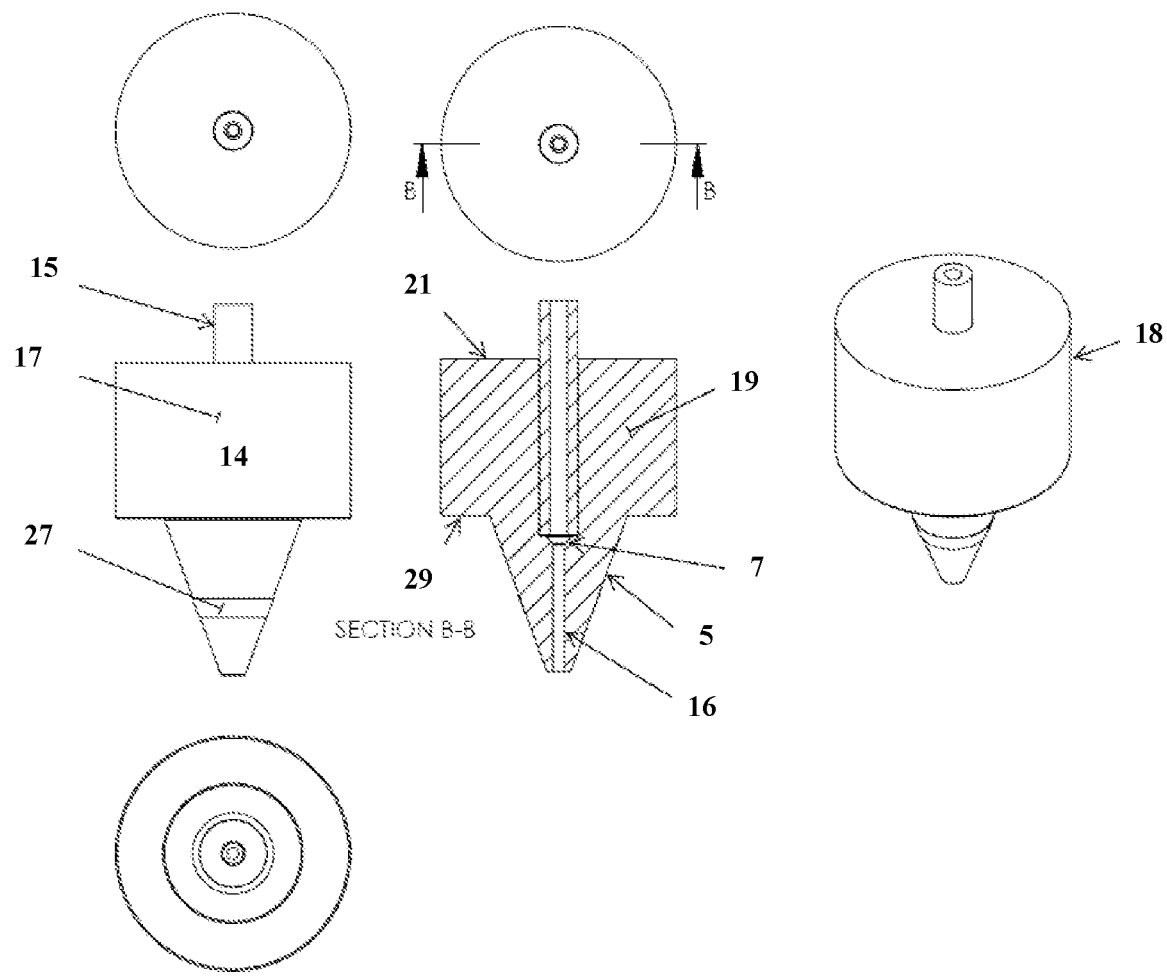

Referring to FIG. 1*d* the primary functioning element of the present invention evidences a nozzle 18 utilized for the purpose of depositing or extruding liquid material onto the surface of the build substrate or mandrel 32. The nozzle 18 will serve as the functional element consisting of a liquid material dispensing system were liquid material is deposited, through cylindrical tube 6 onto the build substrate or mandrel surface 32. Such a system may also be referred to as an extruder or specifically, an extruder of polymer materials. Attached to the nozzle is an apparatus to feed material through the nozzle 18. The present invention may take the form of a controlled displacement piston device, a pressurized pneumatic piston, a screw type extruder, a refillable syringe, or a disposable syringe. Moreover, the material dispensing system may be separated into two parts through necessity where one part supports the flow of liquid material in the form of 2-part adhesives, 2-part curable polymers, UV cured materials, and other liquid materials (e.g. where the base liquid polymer and its liquid activator must be kept separated until the time of use).

For purposes of describing the invention we shall describe the material as UV-LSR (ultraviolet cured liquid silicone rubber). The nozzle 18 may have the configuration of a material jetting device. The means of attachment to the material delivery system 15 may be a threaded nipple or barb type hose fitting to allow for attachment to the liquid material supply system 18. Also, there shall be a provision to attach the nozzle 18 to the motion control system to guide and facilitate the control a direction of the nozzle 18.

Directional movement is further complemented through light curing where light 6 transmission features are integrated into the liquid material supply system 18 nozzle body 19 which may be constructed of clear quartz, cubic zirconia, sapphire, or other clear material suitable for transmitting light and having necessary durability. The metallic inner tube 15, may be constructed of stainless steel and is inserted within the nozzle body 19 existing from above the nozzle top surface 21, through the nozzle body 19, to the base 7 of the conical portion 5 of the extruder at a point of communication past the connection of nozzle body 19 and conical portion 5 at connection point 29. The outer circumferences are surrounded by metallic bands 17 and 27. The top surface 21 and bottom surfaces 29 of cylinder 14 are transparent. The top surface 21 is made to interface with a UV light source (not depicted) and conduct the UV light into the nozzle 18. The bottom surface 29 would allow for light transmission 6 to the build substrate to allow for continuous curing of UV-LSR after liquid extrusion material has been deposited. The conical section 5 would be coated or covered so as to mirror the inside surface of the cone. This conical mirrored surface would direct and concentrate UV light on the LSR material in the final transparent tube section 16 thus initiating the curing cycle of the material before it is deposited or extruded onto the build substrate or mandrel 32.

In another preferred embodiment, it is conceived that light may need to be introduced to the extrusion material further upstream of the liquid material supply system in order to promote sufficient curing by the time material is deposited onto the build substrate. In this version, such a means of introducing light would be achieved in a similar manner to the previously disclosed liquid material supply system, yet the design would use a suitably transparent material for the fluid path and a light source about that material path and a means of conducting and concentrating the light from its source to the fluid flow path using established optical design methods that either varies the temperature degree, intensity, or starting distance of the curing light (or a combination thereof) which would in turn allow for a modification of the curing rate (e.g. beginning the light source earlier in or later in the process, modifying the intensity of the light production, adjusting the medium through which the light must travel, changing the reflection of the light, etc. . . . ).

Perhaps the most crucial component, the fluid material used to build the device that is the present invention, is controlled by a liquid material supply system nozzle 18 that is fed by any number of extruder types (including, but not limited to, screw type extruder, controlled piston type extruder, or similar apparatus to control dispensing volume, material shot size, droplet size, and deposition volume). Manifestly, one or more nozzles/extruders (i.e. deposition heads, or coextruders) may be employed in the apparatus to build the intended device.

It is an anticipated possibility that material may cure prematurely in the nozzle 18 thereby creating a blockage or plug. In this case, a material extruder or material extruders may be incorporated with sufficient pressure or positive displacement force capacity to force overly cured material from the nozzle into a material waste station 9. Alternatively, or in addition, the material delivery system may incorporate solvent delivery and a solvent cleaning cycle to clear the nozzle. Such solvent will be capable of breaking down or dissolving the hardened material.

Equally, thermal control may be incorporated into the nozzle/extruder via metallic band 17 and band 27 which may be temperature controlled, heated, or cooled, for the purpose of material delivery and curing process control. Similarly, the delivery tube 15 may be temperature controlled. Conventional electrical thermal control systems will be employed for this provision. Such systems utilize heating elements which are made of a metallic material of adequate electrical resistance so as to generate heat when an electrical current is passed through it. Delivery tube 15, band 17 and band 27 may be used as heating elements in this sense, or may be integrated with heating elements or bands suitable for incorporation into the nozzle 18 or about the fluid path.

Different nozzles 18 with different inner tip diameters 16 will be utilized depending on the dimensional and precision requirements of the filament diameter to be extruded. Moreover, each nozzle 18 may incorporate a spherical, conical, or needle seat type gate valve 7 so as to prevent the backflow of cured material and contamination of uncured material.

Figure 2A:
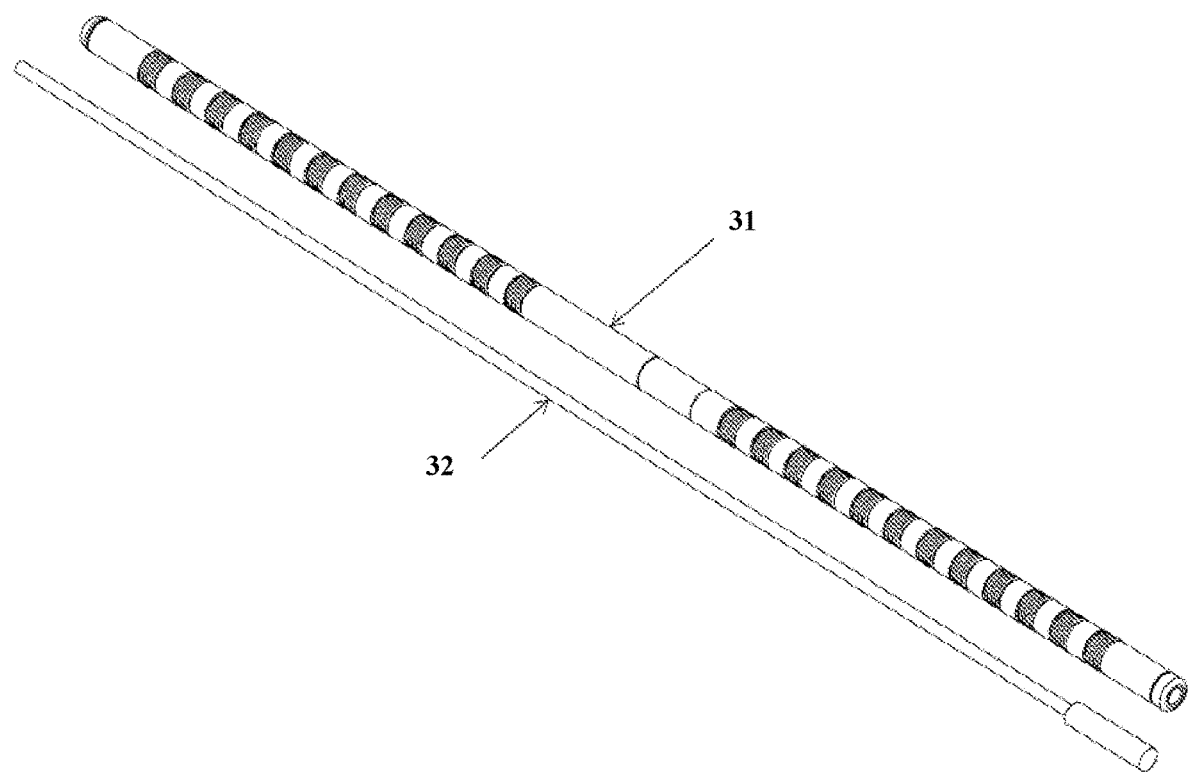
FIG. 2a shows an example of a completed assembly representing the present invention with a configuration of a #3 French 12-conductor lead with the build substrate rod removed.

Referring to FIG. 2a, a finished device 31 is depicted for use as a neurological electrical stimulation or signal recording device with leads and electrodes where a finished 12-conductor, 12-electrode lead for neuro stimulation or neuro recording is of a 3 French catheter size (having an outside diameter of 1.0 mm (Fr 3=1.0 mm dia.)). The device 31 is modeled and illustrated to demonstrate the implementation of this invention in one of the simplest configurations where each connected or contiguous contact, conductor, and electrode assembly shall constitute a single electrical channel in the device where device 31 may be called a 12-channel lead. Yet, as well, there are nearly infinite configurations conceivable by manipulating achievable geometries with the build apparatus. A substrate is also represented in the form of a cylindrical mandrel 32 which serves as a build substrate and is shown removed from the device/lead body. The build substrate or mandrel 32 is removed in a post-process once the build is complete.

Figure 2B:
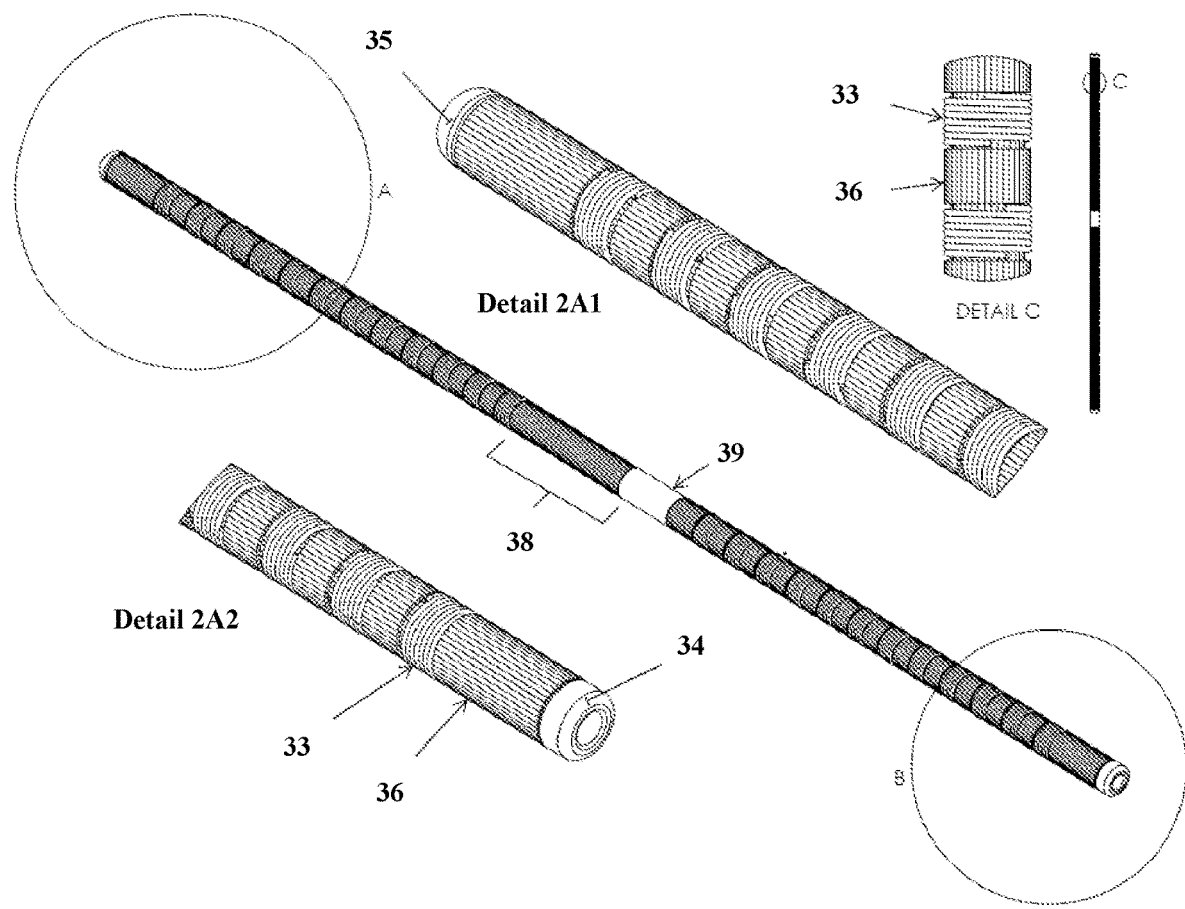

A 12-electrode lead is illustrated in FIG. 2b evidencing the product of a method where filaments are deposited onto a rotating substrate, build platform or mandrel which is typically cylindrical, but may be of other simple or complex geometries. These filaments are deposited by extruding a liquid polymer or silicone rubber material in a typical additive manufacturing process. Visible in details 2A1 and 2A2 are filaments (both conductive and non-conductive) that are deposited longitudinally or wound circumferentially where A designates the forward tapered front lead tip and B the lead end capable of connection. Other filament directions, paths, and shapes are possible other than these shown.

Though, unique to the invention is the method by which liquid polymer or liquid silicone rubber (LSR) material can be deposited and cured in a controlled manner so as to achieve the dimensional and geometric requirements for the devices described herein.

Succinctly, the 12-electrode lead illustrated has a general construction configuration utilizes 4 layers of material deposited circumferentially about the mandrel (as depicted in FIG. 2a, build substrate or mandrel 32).

A combination of conductive polymers 33 and nonconductive polymers 36 are constructed using a liquid polymer with conductive properties, in the case of conductive polymer 33, and non-conductive properties, in the case of nonconductive polymer 36. Metallic components are shown inserted which are not part of the electrical circuit path: first substrate end 34 (designated in B), second substrate end 35 (designated in A), and metal band 39 where first substrate end 34 functions as a stylet guide, second substrate end 35 is a blunt or bullet end which is radio opaque as a lead placement marker which serves as a stop for the stylet and helps to guide the lead when threaded through catheters or tissues. Item 39 is a metal band used as a setscrew seat for traditional cylindrical connector fixation methods.

Each of these components shown (substrate end 34, substrate end 35, and metal band 39) are separate metallic inserts which are integrated into the device during the build process. Alternatively, all of these components may be formed integrally in the device using additional polymer materials of sufficient final durometer or hardness which are deposited during the build.

Metal band 39 is shown close to the connector body end or proximal end of the lead. Lead body 38 is shown very short for illustration purposes. In practical application this lead body 38 can be of considerable length and constitutes the majority of the device length.

For conductive and nonconductive portions of the insertable lead, conductive properties for polymeric conductors 33 (and electrodes) are achieved using carbon nanotubes of single-wall (SWCNT) or multi-wall (MWCNT) configuration blended with the polymer material where the blend of SWCNT or MWCNT shall be varied or optimized to achieve ideal electrical properties and performance for the intended applications and non-conductive polymers 36 are formed utilizing non-blended polymer, pure polymer, or the "base polymer" and shall have sufficient electrical insulating or dielectric properties such that it will be used to form the insulating components and features of the device.

The base polymer material may be a formulation of liquid silicone rubber (LSR), urethane, or epoxy materials either singularly or blended such that said materials may be two parts or two fluids, base and catalyst or activator, or a combination thereof, to achieve curing to the final state. Such formulations will be developed to achieve ideal properties for the intended application and may need to cure to transition from its state of flow for deposition into its final hardened state where the final state shall have some degree of flexibility which may be varied by chemical and process controls to achieve desired properties for the intended application.

In terms of curing, the LSR material (or other base polymer) suitable for intended applications may be cured using light energy, thermal energy, or ultrasonic vibration, or a combination thereof, as desired. If light energy is used, it shall be of a wavelength suitable to cure the polymer formulated for the final application of the device having a wavelength ranging from the infrared (IR) to the ultraviolet (UV). Although light ranges may vary, for descriptive purposes of describing the invention, we shall use UV cured LSR (UV-LSR) as the light wavelength and base polymer for conductive material to form combination of conductive polymers 33 and nonconductive polymers 36. But, this described use of UV-LSR for device construction is not intended to exclude other possible polymers or conductive polymeric compounds which through research and development may prove ideal for human implantation, biocompatibility, chronic use, and service longevity.

Figure 3A:
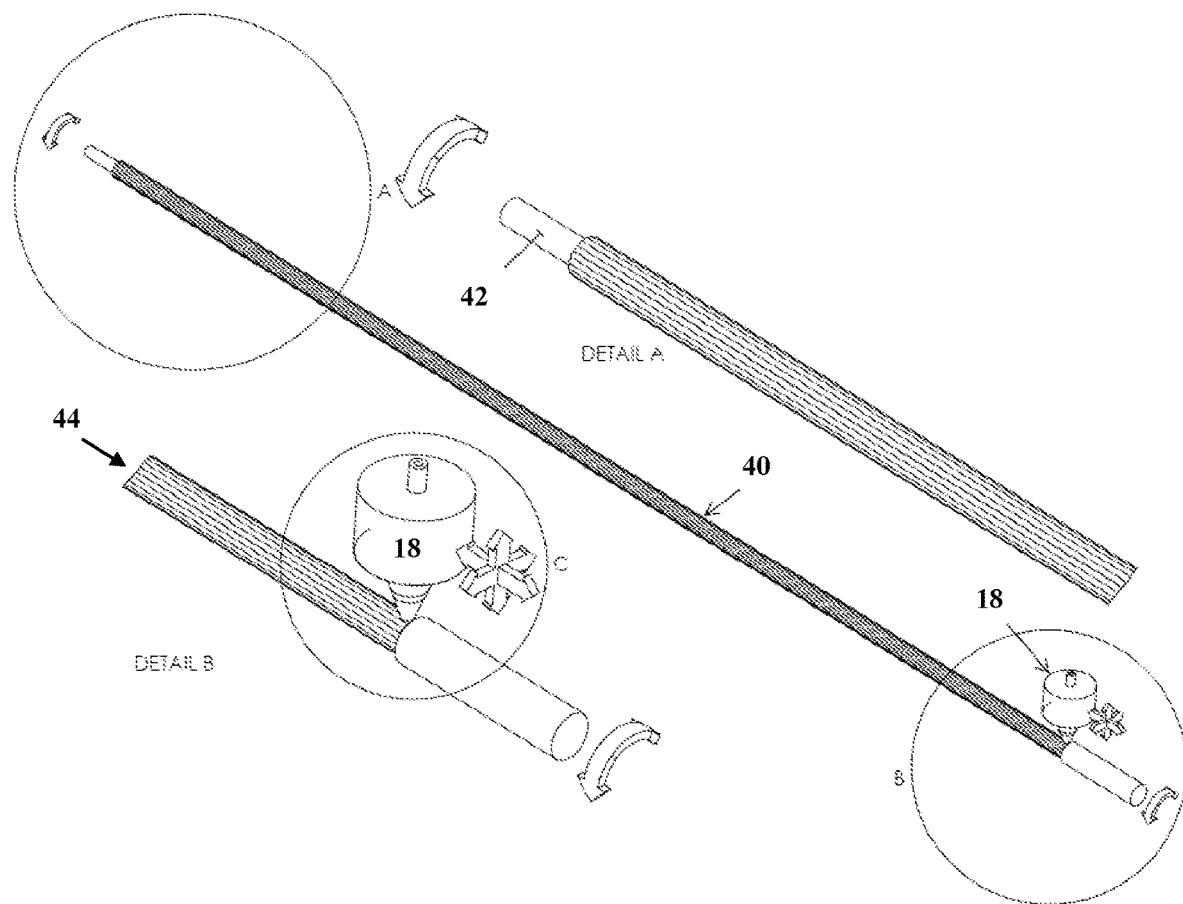

The sequence of building a lead is shown in FIG. 3a by deposition or application of the first layer of material 40 along the length of the mandrel substrate 42. The deposition nozzle 18 is represented as able to move in 3 planes (X, Y, and Z planes) and rotate in up to 3 axes (axes A, B, and C). The first layer of representative UV-LSR is deposited as a bead of material in the shape of filaments along the length of the mandrel 42 in the X direction. The location, length, and geometric path for these filaments are programmed by means of a graphical 3-dimensional model of the device. As in any other additive manufacturing process, the model in converted to a data file suitable to numerically control the manufacture of the product.

After each filament length 44 is deposited, the mandrel 42 is rotated in the theta axis (Ø) an arc length equal to the filament diameter. Thus, the next filament length 44 is placed immediately next to (and contiguous with) the previous one, and so forth, until the mandrel is completely encapsulated in LSR. For reference, in this example device, there are 18 filaments required to encapsulate the mandrel in this first layer of filaments, or application; the mandrel in this example is approximately 0.4 mm in diameter (but of course could be larger or smaller); and each filament is approximated as circular in cross section with an approximate diameter of 0.08 mm. All filaments in the first layer are made with nonconductive LSR (NCLSR). For this layer the head will need to move in axes X and Z (not Y) and the mandrel 42 rotates in axis Ø. The other motion control axes can be used for more complicated geometry than is necessitated for this example device.

Figure 3B:
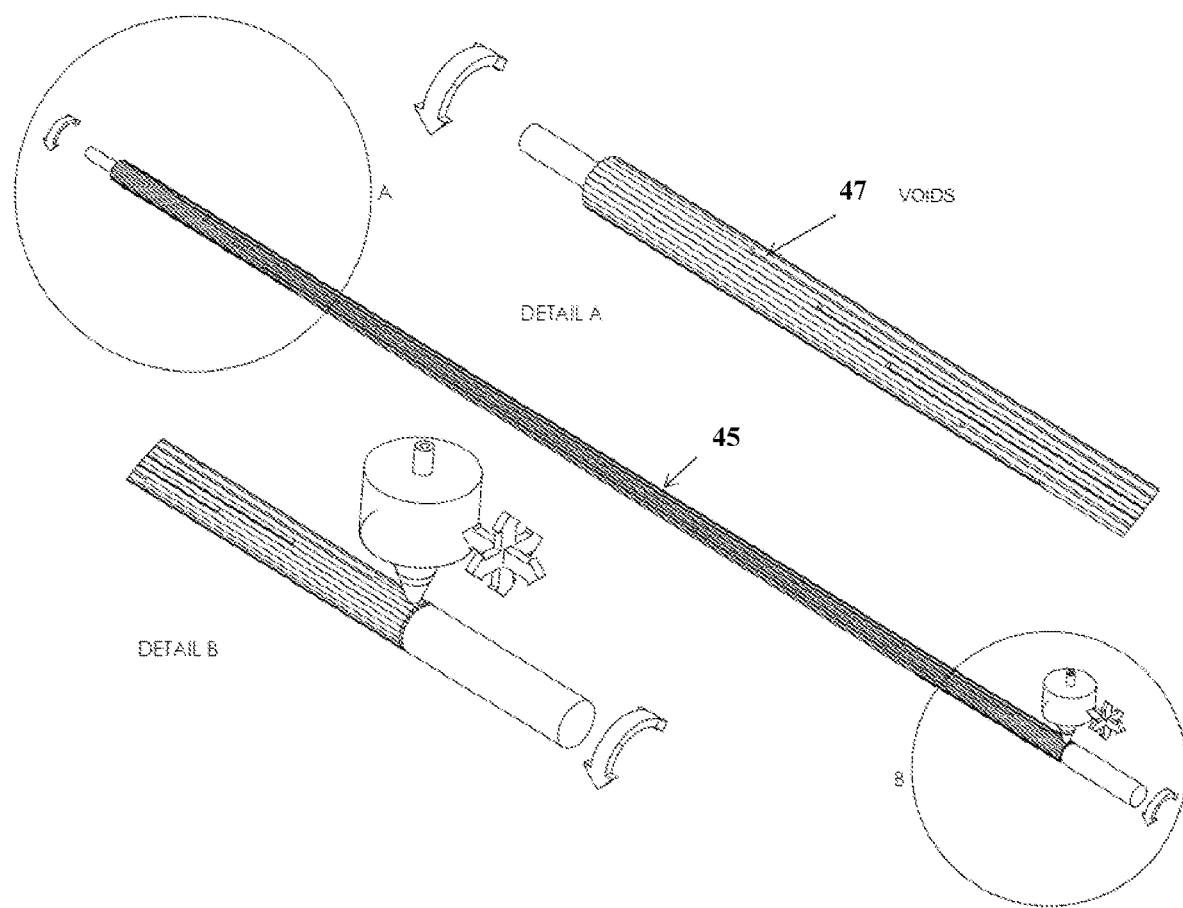
FIG. 3b illustrates the second application layer of construction.

Next, Referring to FIG. 3b, the second application layer of NCLSR 45 is deposited in the same manner as the first layer. For reference, 24 longitudinal filaments or passes of the deposition head will be required to complete the second application layer of NCLSR. Voids 47 are left longitudinally in key locations to allow for deposition of conductive LSR (CLSR). CLSR is will be deposited where there are voids 47 in this second layer 45.

The build sequence exhibits alternating deposition NCLSR and CLSR to produce a completed device that has alternating polymers of conductive and non-conductive material that may or may not occur at repeating intervals, non-repeating intervals, or sequentially and non-sequentially repeating intervals (here depicted as regularly repeating intervals, yet the sequence may be varied to optimize the manufacturing process and may differ from the sequence presented herein for the simple purpose of defining the invention). As well, the apparatus for manufacture may contain one or more deposition heads/nozzles and segregated material delivery systems, one for NCLSR and one for LSR, and a means for incorporating other materials necessity dictates.

Figure 3C:
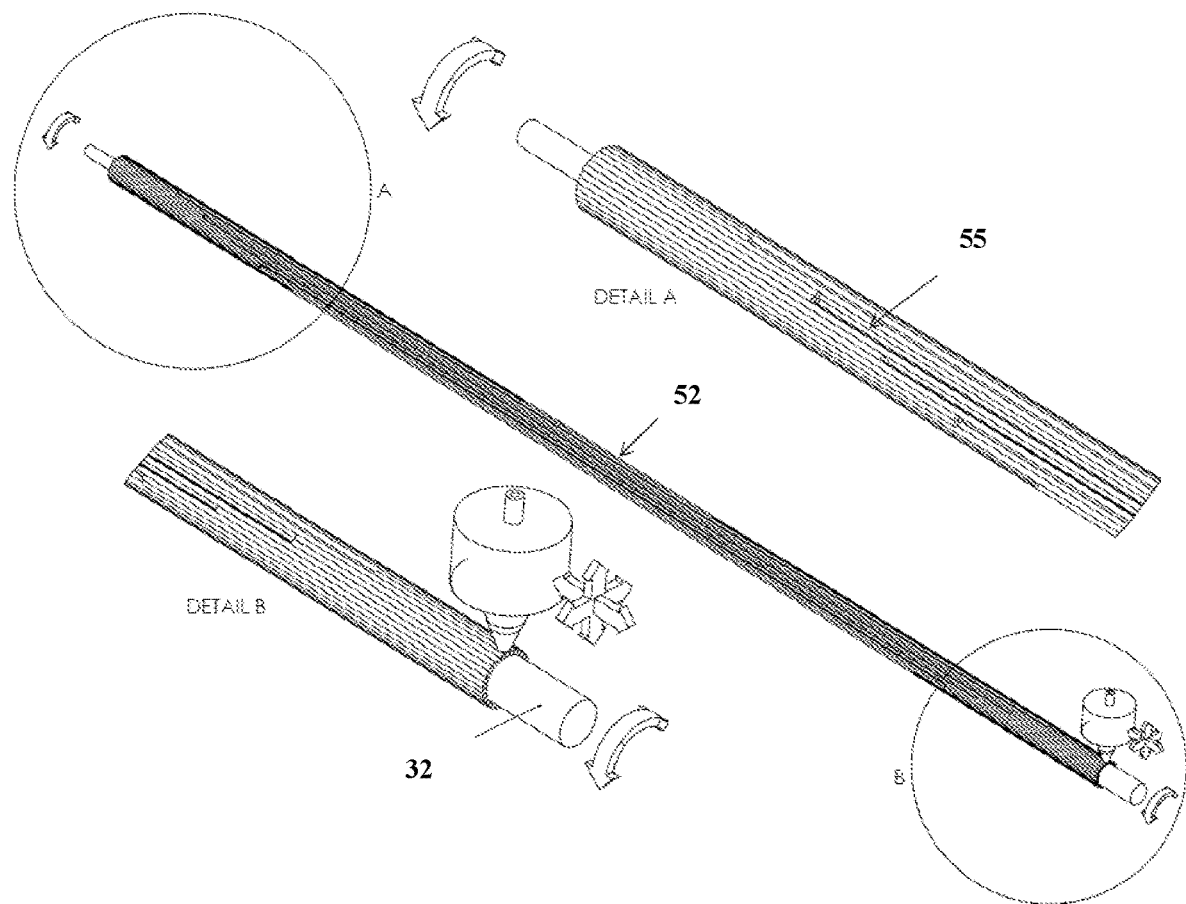

FIG. 3c, represents a third application layer of NCLSR filaments 52 which are deposited in the same manner as the second layer (including voids 55 left where CLSR will be deposited). The voids 55 in this layer, layer three 52, are smaller than the voids 47 of the second layer. The CLSR deposited in these voids will act as radial pathways.

Figure 3D:
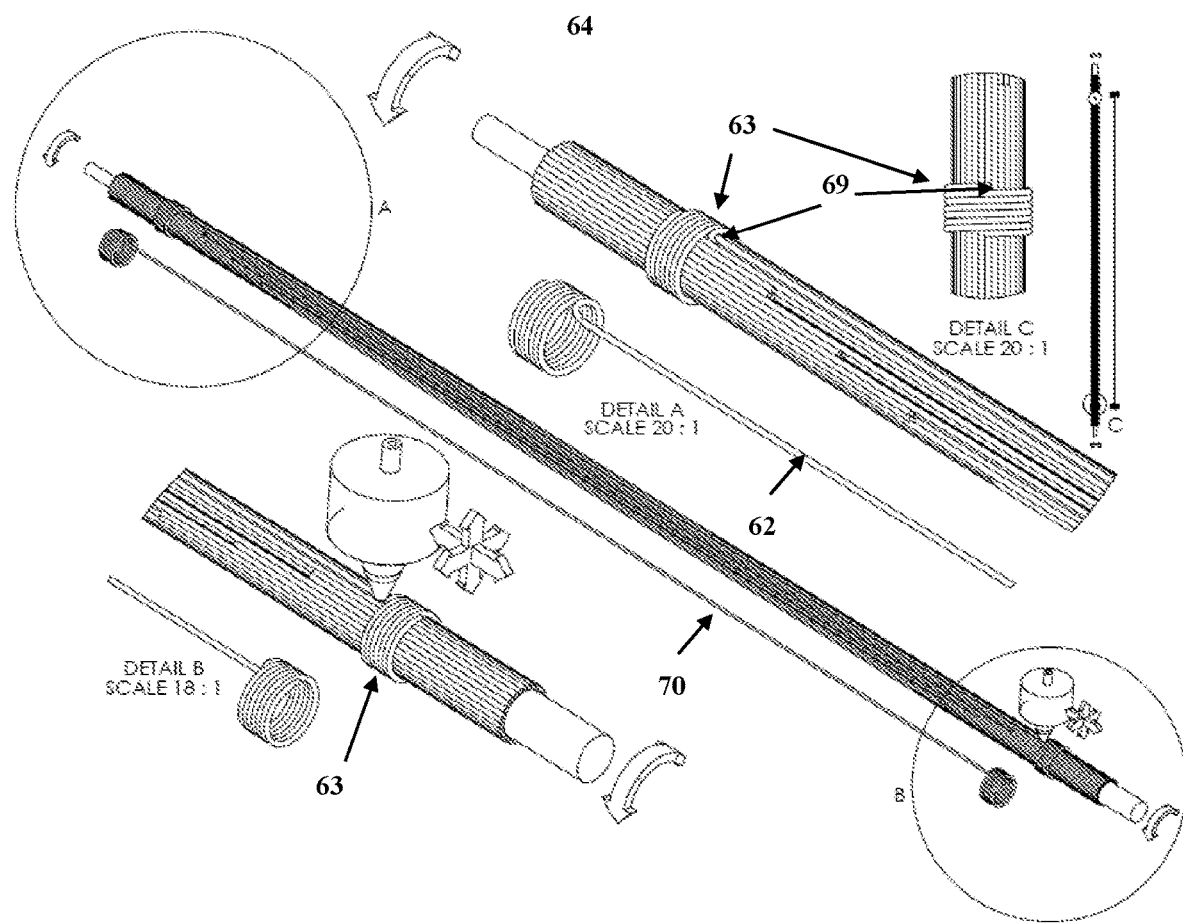
FIG. 3d illustrates the construction of the first of 12 electrodes (Electrode 1) contained in the device.

Referring to FIG. 3d, a 4th application layer 64 begins by depositing CLSR in single continuous element 70 comprised of coiled 63, radial 69, and longitudinal filaments 62. The coiled band at the distal end of the lead will serve as an electrode. The coiled band at the proximal end will function as a contact feature for an electrical connection with the signal generating or recording apparatus. Together, this group of continuous conductive filaments 70 constitutes a single conductive element, circuit path, electrical channel, or pathway of homogeneous material.

Figure 3E:
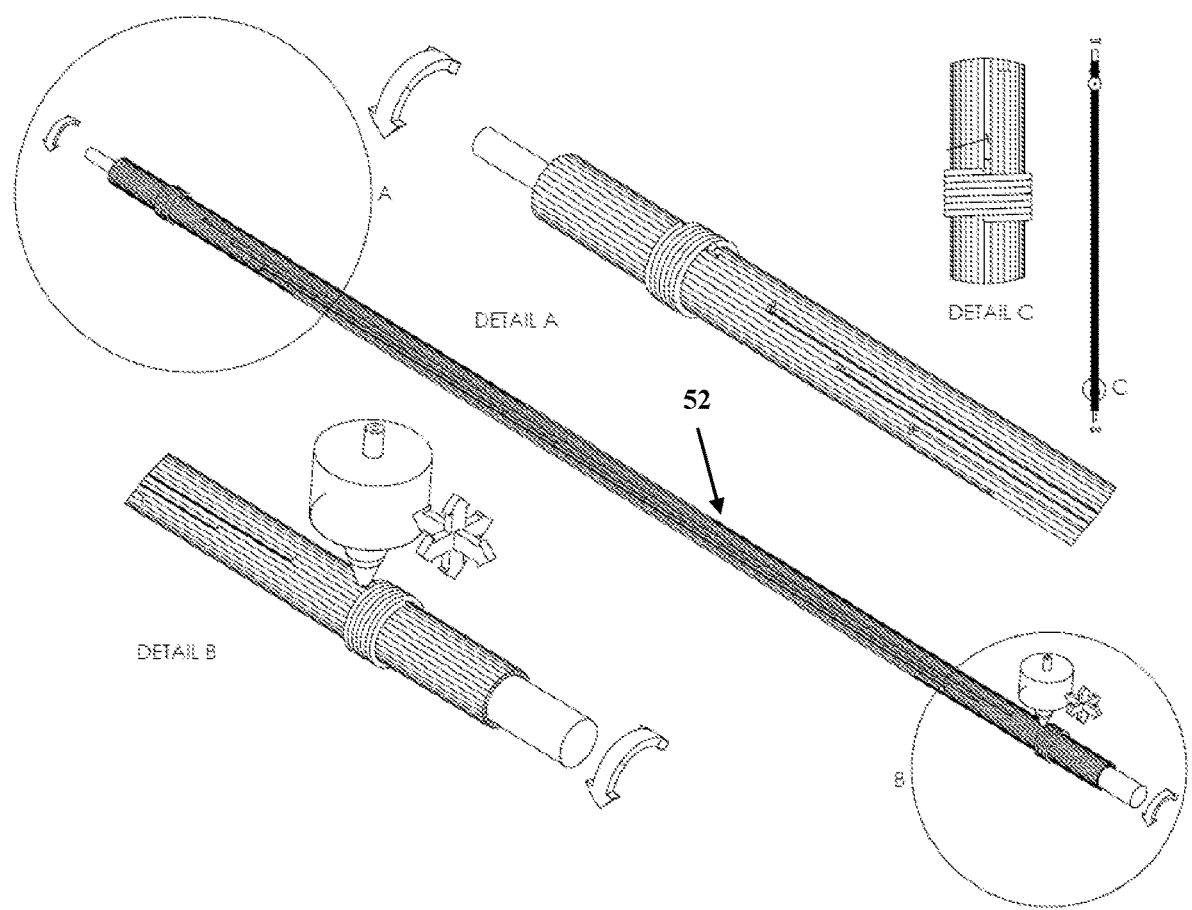
FIG. 3e illustrates the construction of the insulating cover for Electrode 1.

Referring to FIG. 3e, conductive filaments are covered with NCLSR in the $3^{rd}$ application layer 52.

Figure 3F:
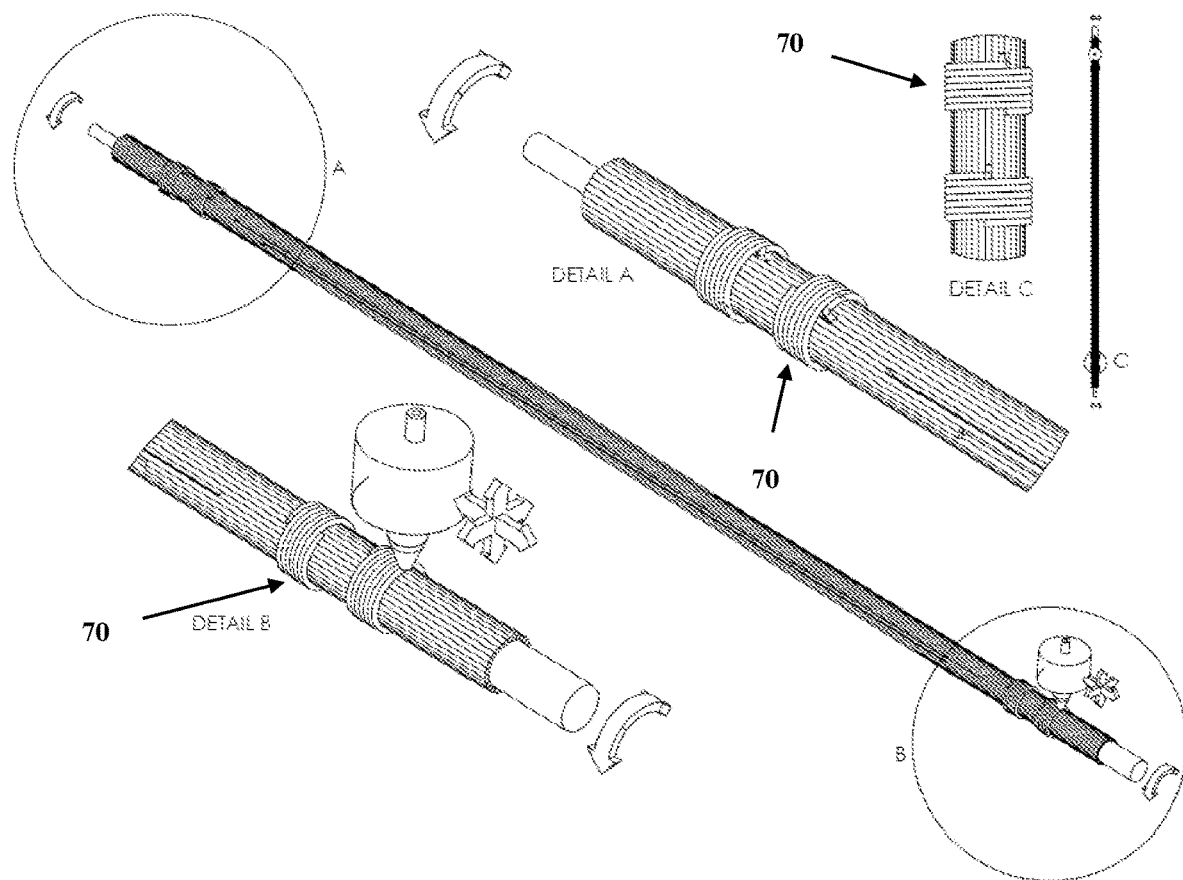
FIG. 3f illustrates the construction of Electrode 2.

Referring to FIG. 3f, the construction of the second of 12 conductive elements 70 is represented.

Figure 3G:
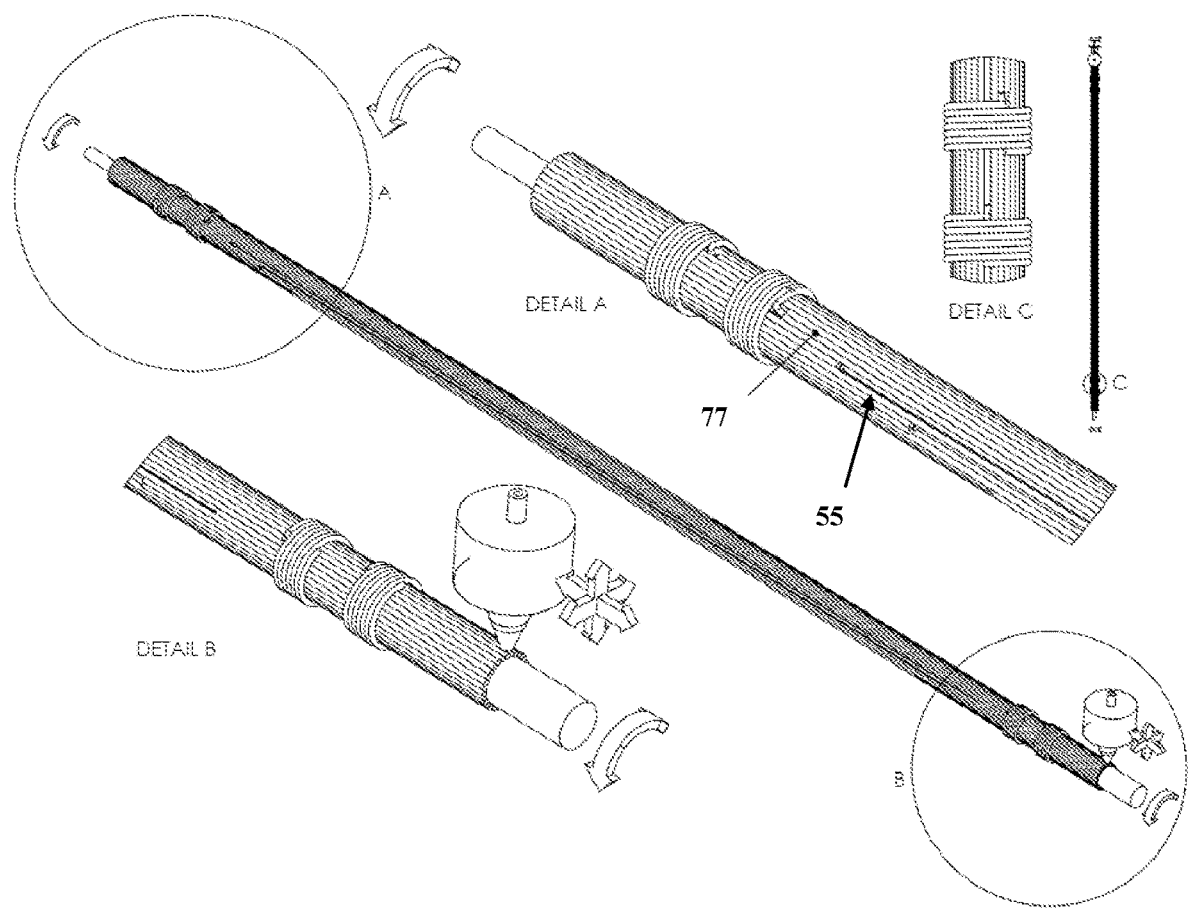
FIG. 3g illustrates the construction of the insulating cover for Electrode 2.

Referring to FIG. 3g, NCLSR is again shown being deposited 77 in the 3rd application layer 52 including voids 55 to cover the longitudinal filament for the second conductive element 70.

Figure 3H:
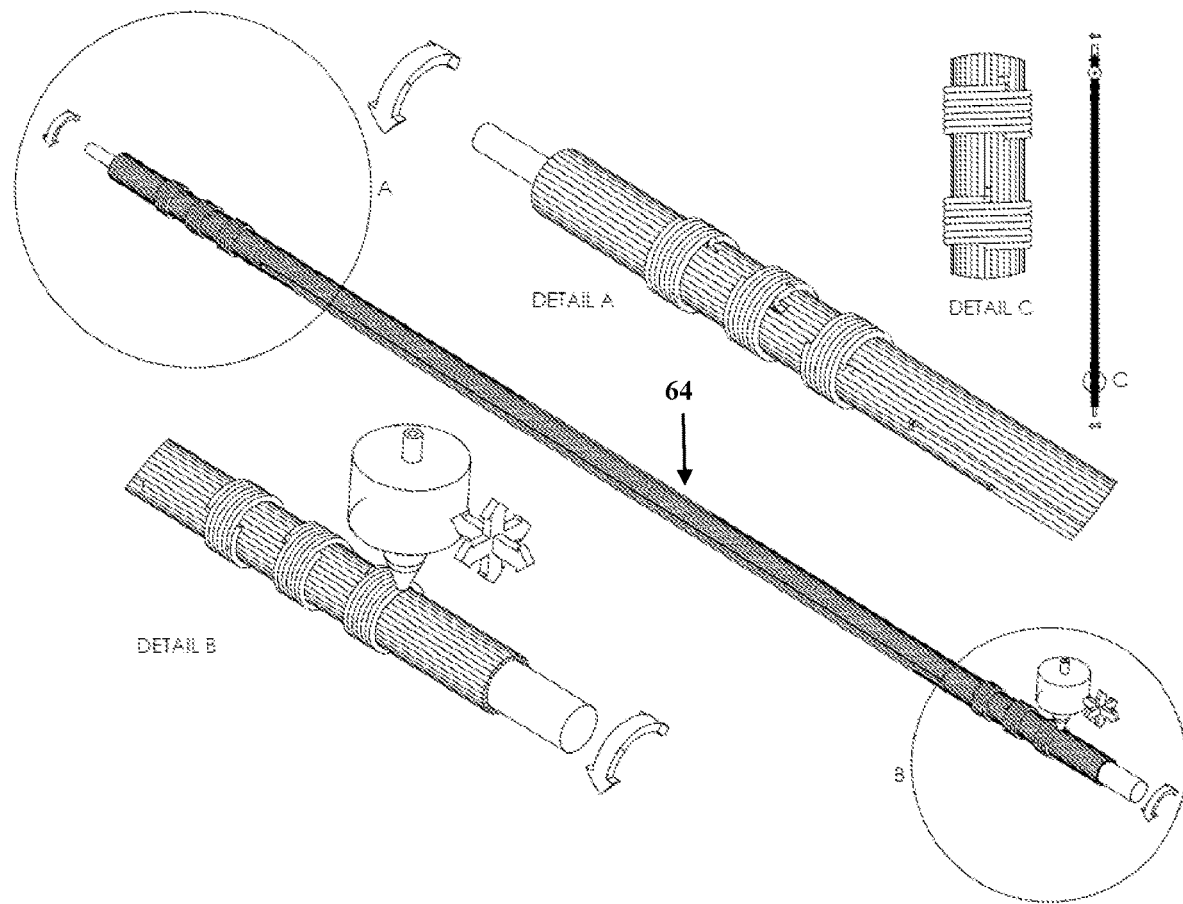
FIG. 3h illustrates the construction of Electrode 3.

Referring to FIG. 3h, a 3rd conductive element 70 in the $4^{th}$ application layer 64 using CLSR is shown for clarity of build sequence.

Figure 3I:
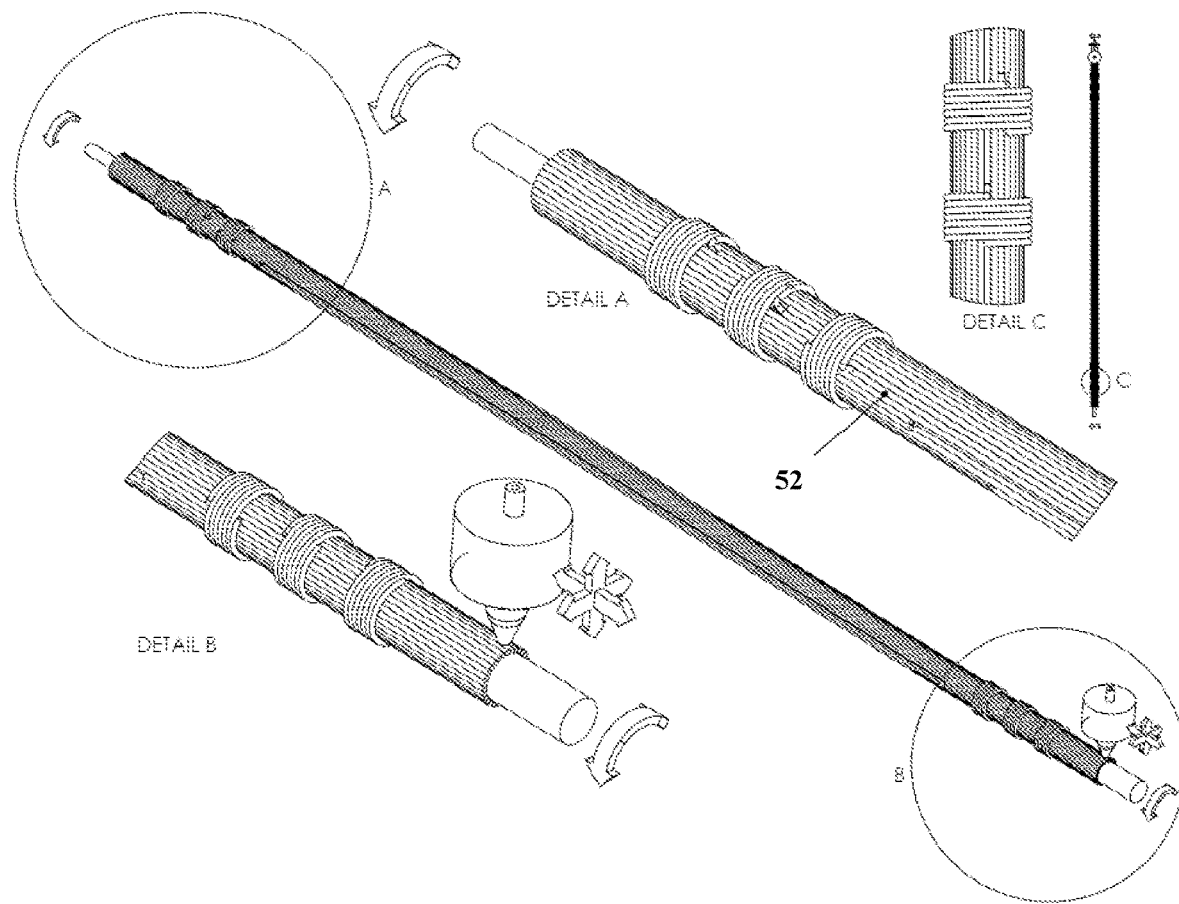
FIG. 3i illustrates the construction of the insulating cover for Electrode 3.

Referring to FIG. 3i, the 3rd electrode longitudinal cover deposition of NCLSR in application layer 3 52 using NCLSR is shown for clarity of build sequence.

Figure 3J:
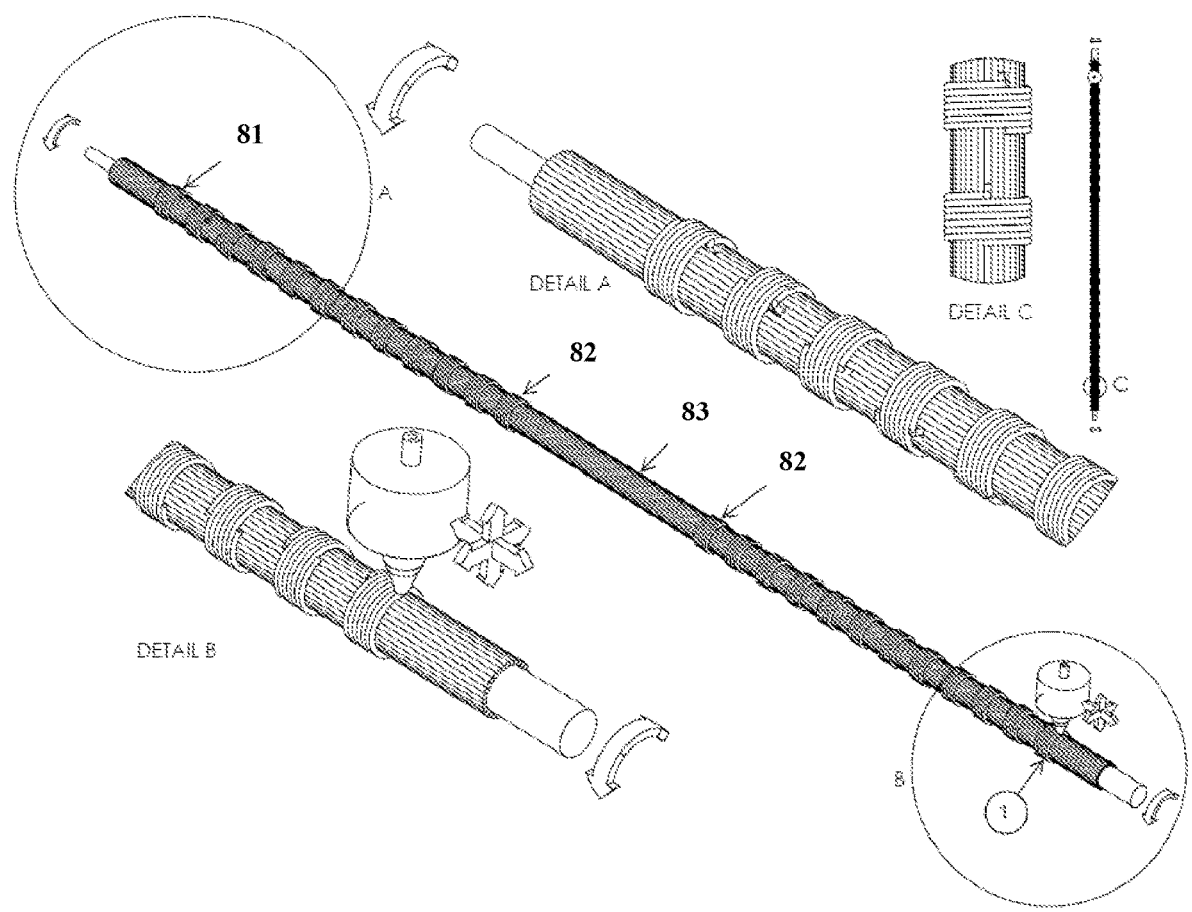
FIG. 3j shows all 12 electrodes for the example device constructed in place on the assembly.

Referring to FIG. 3j, all 12 electrodes from channel 1 81 to channel 12 82 are shown deposited on the incomplete lead body 83.

Figure 3K:
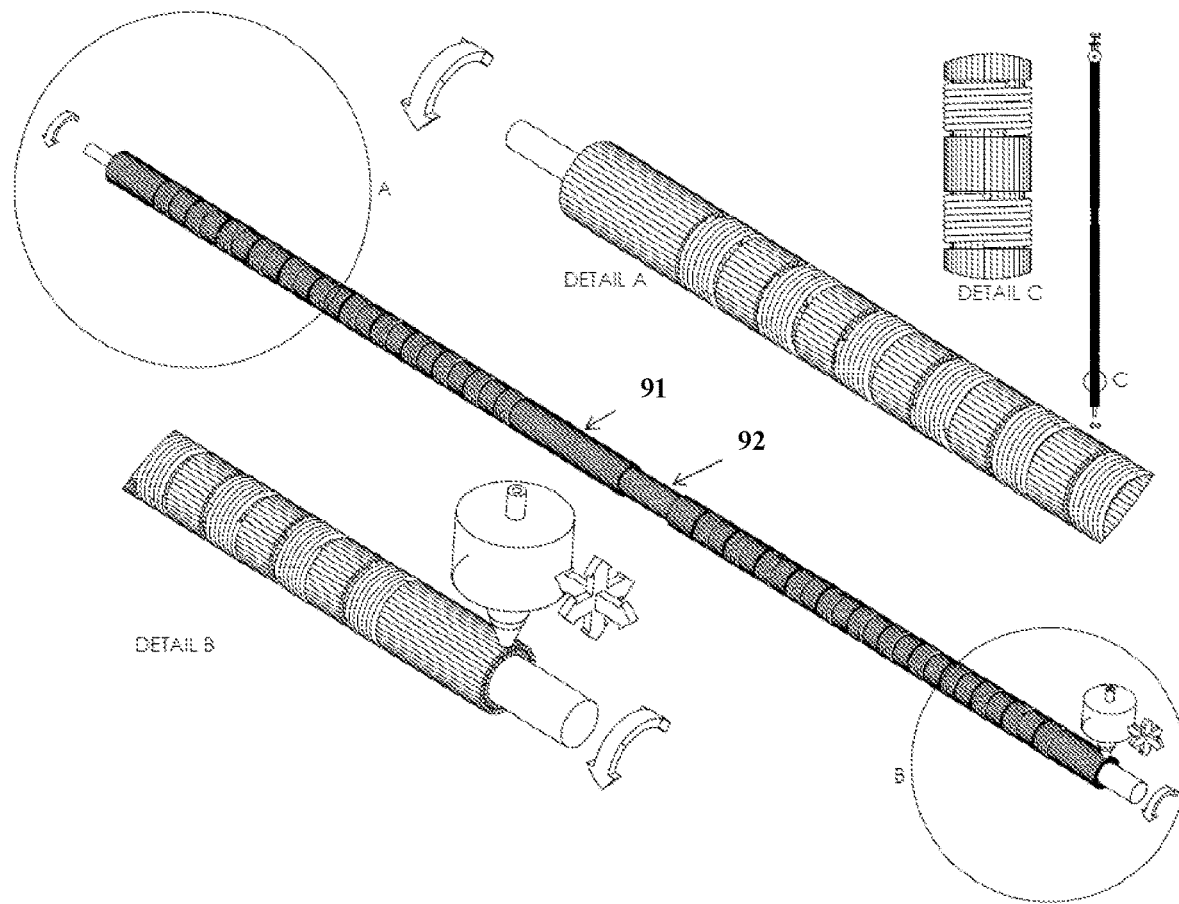
FIG. 3k illustrates construction of the insulating cover for the final assembly.

Referring to FIG. 3k, a final cover of NCLSR is deposited to completely cover all remaining areas of layer 4 64 not occupied by CLSR and to complete the outer dimension of the lead body 91. Voids in the shape of a band 92 or other voids may be left in this 4th and outer layer 64 for the provision to add functional components or materials of differing hardness to the exterior. The example shown shall be for a band which functions as a set screw seat 39.

The final assembly is depicted in FIG. 2a and FIG. 2b illustrates a final functioning device with all components deposited or installed and with the mandrel 32 removed.

Figure 4:
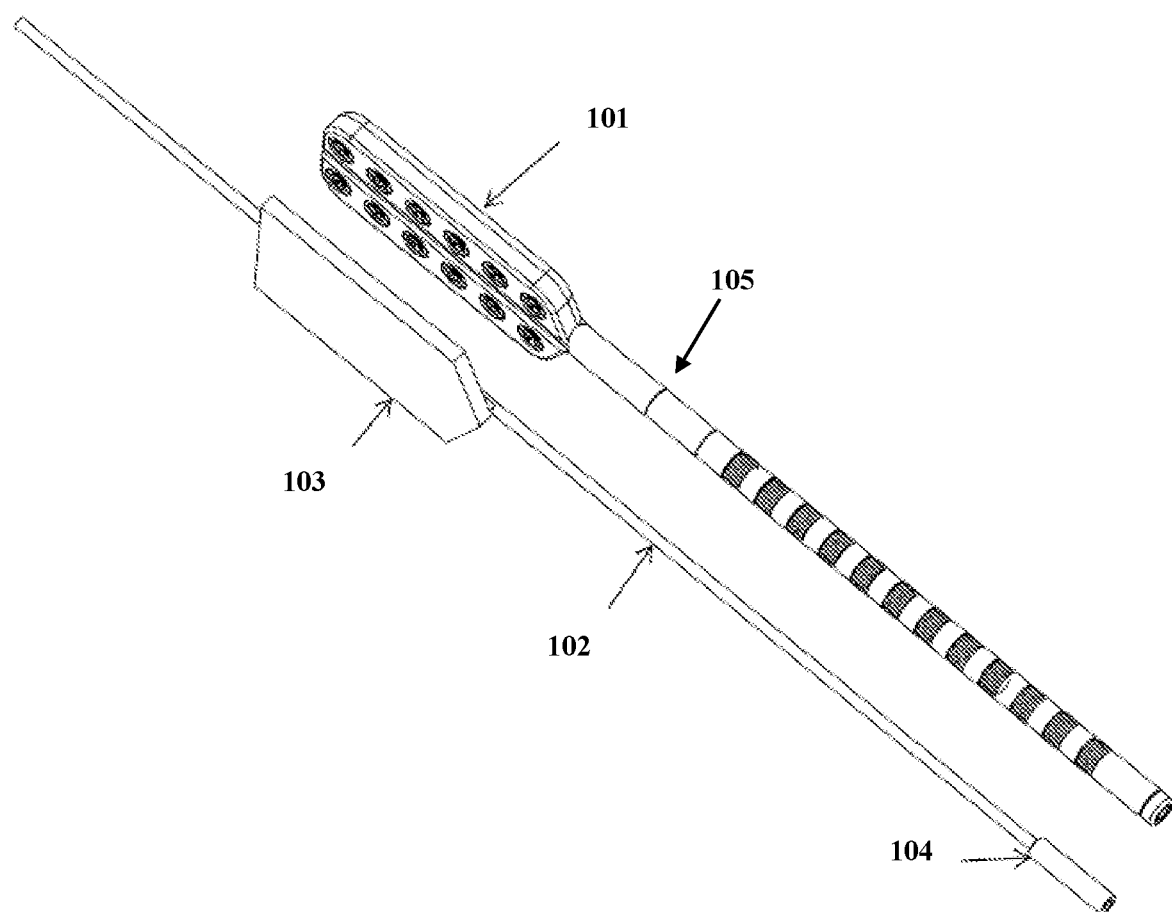
FIG. 4 illustrates a final device with 12 electrodes arranged in a flat "paddle" configuration and corresponding build substrate.

FIG. 4 evidences a "paddle" electrode 101 illustrated with 12-channels or contact pads on the distal end 105 or "paddle" end of the lead 31. The geometry of a 12-electrode lead device represents a common configuration for neurologic stimulation and recording applications. It is depicted to illustrate the flexibility of the apparatus to produce other configurations. To produce this device using the apparatus described herein, a augmented mandrel apparatus 102 is conceived having a flat planar build section 103 integrated with the augmented mandrel apparatus 102. The augmented mandrel apparatus 102 may require a removable shank at the proximal end 104 and the flat section 103 may be constructed from the same material as the cylindrical mandrel 32.

Alternatively, the flat section 103 may be constructed of a dissolvable scaffold material where such material would be dissolved in a secondary process after the completion of the build and will not be part of the final device assembly. Such a technique is common practice in additive manufacturing.

Figure 5:
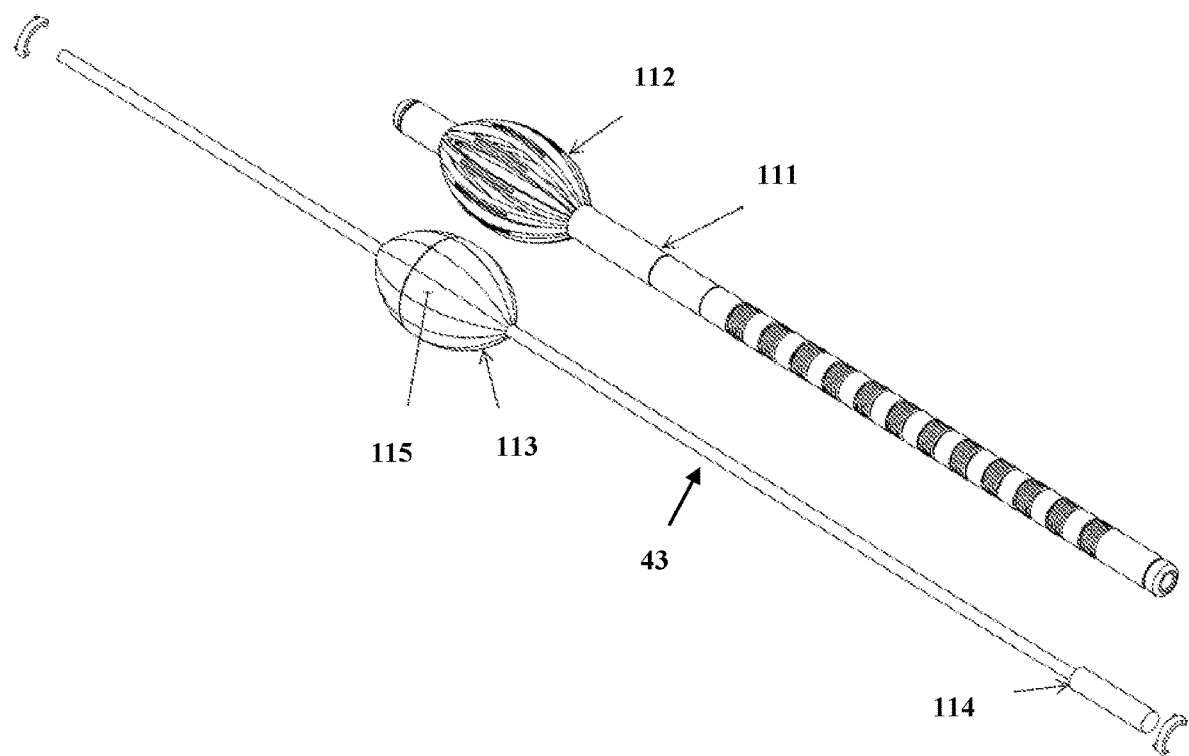
FIG. 5 illustrates a final device with 12 electrodes arranged in a unique stent-electrode or "stentrode" type configuration and corresponding build substrate.

FIG. 5 advances a unique geometry for a 12-channel electrode (e.g. a stent-electrode or stentrode 111 having an electrode arrangement as shown, or the individual electrode branches 112 may be formed in a helical pattern. To facilitate stentrode 111 placement, the helical twist may be the same direction for all 12 electrodes, or a portion of electrodes may be twisted in the opposite direction. Equally, a bulbous build substrate or scaffold 113 may be integrated with the modified build scaffold 43 similar to the integrated mandrel in FIG. 4. The modified build scaffold 43 may require a removable shank at the proximal end 114.

This build scaffold may be made from dissolvable material, which may be deposited in segments or wedges 115 where such material may be dissolved in a secondary process after the completion of the build and will not be part of the final device assembly.

Figure 6:
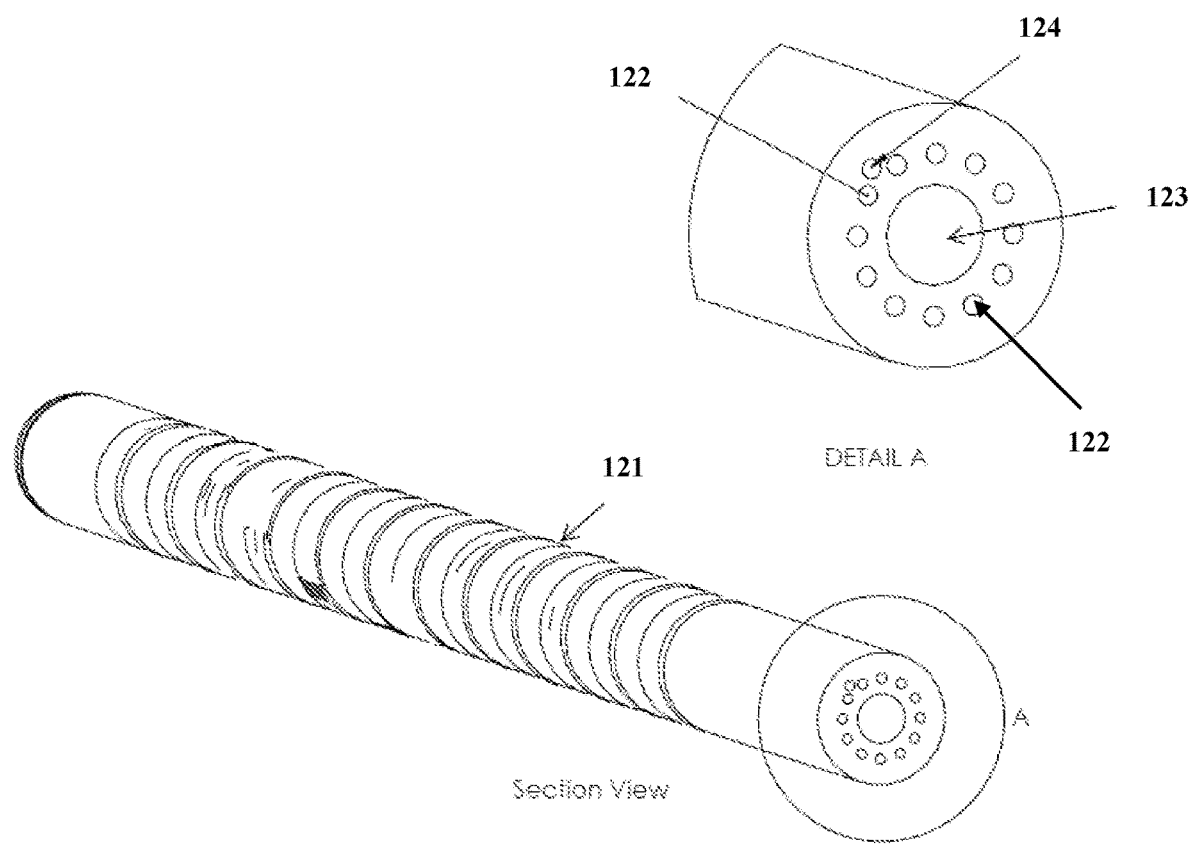
FIG. 6 illustrates a sectional view of a final device where there has been created an additional void, channel, or tubular structure within the device.

FIG. 6 provides a cross-sectional view of a completed device lead body 121 with the modified build scaffold 43 removed and showing the electrode conductors 122 the resulting hollow core 123 which may act as a tube for fluid delivery applications. In this example of a completed device a tubular feature 124 may be added which may be a void, hollow cavity, or tube which runs the full length or a partial length of the device. While only represented as one such cavity, tube or void, such voids, cavities, or tubes may be several in number within the device. These tubular features 124 may be configured to extend to the outer or inner circumference of the device thus connecting radial voids with longitudinal voids, as one example, either of these features (hollow core 123 or tubular feature 124) may be used for a clinical application such as drug delivery channels, fluid distribution mechanisms, light dispensing modalities, or a combination thereof.

The foregoing descriptions of the embodiments of the present invention have been presented for purposes of illustration and description. They are not intended to be exhaustive or to limit the present invention to the precise forms disclosed. The exemplary embodiments were chosen and described in order to best explain the principles of the present invention and its practical application, to thereby enable others skilled in the art to best utilize the present invention. Although specific embodiments have been illustrated and described herein, a variety of alternate and/or equivalent implementations may be substituted for the specific embodiments shown and described without departing from the scope of the present invention. This application is intended to cover any adaptations or variations of the embodiments discussed herein.

What is claimed is:

1. A method for fabricating an electrical conducting lead for electrical current generation and signal recording comprising the steps of:

a. extruding through a depositing nozzle a polymeric material, either conductive, non-conductive, or alternatingly both conductive and non-conductive polymeric material, in an additive manufacturing process onto a moveable build substrate;

b. firstly, depositing non-conductive extrusion polymeric material in such a form as to allow for a continuous, homogeneous initial application along the length of a substrate via a nozzle;

c. moving said nozzle in orthogonal directions while rotating the substrate about one or more separate axes;

d. positioning the substrate and adjusting the nozzle's rate of deposition, distance from substrate and position in relation to substrate as to allow each subsequent application to be placed immediately adjacent to or above or otherwise about the previous application as to form a contiguous structure;

e. continuing the process until the polymeric material is adequately adhered to the substrate and/or adjacent polymeric segments either completely or partially;

f. depositing of a second application of polymeric material adjacent to, radially, outwardly or otherwise contiguously adhered to said initial application in a similar manner as the initial application except that voids or gaps of equal size, unequal size, regularly or irregularly occurring sequential, non-sequential, repeating, non-repeating, patterns are created where no polymeric material exists;

g. placing within these voids conductive polymeric material in a predominantly alternating format of sequential, non-sequential, repeating, non-repeating, sequential, and non-sequential patterns as to optimize the placement of conductive and non-conductive elements with no loss of electrical continuity and conduction;

h. depositing of a third application of non-conductive polymeric material leaving voids where conductive polymeric material will be deposited;

i. depositing of conductive polymeric material into the voids of application three wherein the resulting conductive material element is comprised of coiled, radial, longitudinal and/or other geometrical conformations;

j. adhering an outer application of non-conductive polymeric material that is deposited to completely or incompletely cover remaining areas of the prior application not occupied by conductive polymeric material and to complete the outer dimension of the lead body; and k. removing electrical conducting lead from the build substrate.

2. The Method of claim 1, wherein light energy, thermal energy, or a combination thereof is utilized in curing deposited liquid polymer in a time controlled manner, via light or thermal energy, as to allow for hardening for the deposition of subsequent applications.

3. The method of claim 1, wherein one, two, or a plurality of nozzles are used for polymeric material deposition.

4. The method of claim 1, wherein conductive elements are formed that constitute a continuous electrical signal path as one contiguous pathway or channel in the lead.

5. The method of claim 1, wherein voids may be created as a provision for functional components of additional conductive material or materials, metallic or polymeric, of differing thickness, hardness, composition or electric conductivity.

6. The method of claim 1, wherein the build substrate, or a portion or subsection thereof, may be made from removable material, which may provide temporary structural support, or scaffold, for various geometric forms and not be part of the final device assembly.

7. The method of claim 6, wherein the method of removal is accomplished through dissolution of build substrate material.

8. The method of claim 1, wherein the resulting hollow core, or plurality or cores, after substrate removal, may provide for a fluid or light delivery system.

9. The method of claim 1, wherein channels, windows or voids may be created within discrete material applications allowing for a continuous feed of fluid or light transportation that may have one to a plurality of exit points about the device or configured to extend to the outer or inner circumference of the device thus connecting radial voids with longitudinal ones, various channels with coextensive channels, or a matrix of various channels in any number of desired configurations.

10. The method of claim 1, wherein the device is an electrical conducting lead exhibiting a conducting pattern where the linear, helical, serpentine, intertwined, braided, zig-zag, saw-tooth or other configuration of conductive elements may have all pathways functioning in the same direction or opposite directions and generate impulses, receives information, or a combination thereof.

* * * * *